United States Patent [19]
Curry

[11] Patent Number: 4,839,914
[45] Date of Patent: Jun. 13, 1989

[54] PORTABLE TIRE X-RAY APPARATUS AND METHOD

[76] Inventor: Leonard O. Curry, 8363 Nieman Rd., Lenexa, Kans. 66214

[21] Appl. No.: 60,724

[22] Filed: Jun. 10, 1987

[51] Int. Cl.$^4$ ............................................. G01N 23/04
[52] U.S. Cl. ........................................ 378/61; 378/56; 378/58
[58] Field of Search ....................... 378/56, 58, 61, 62, 378/68, 69

[56] References Cited

U.S. PATENT DOCUMENTS

| | | |
|---|---|---|
| 2,220,246 | 11/1940 | Kizaur . |
| 2,301,251 | 11/1942 | Capen . |
| 2,339,550 | 1/1944 | Bosomworth . |
| 3,809,900 | 5/1974 | Steffel . |
| 3,826,919 | 7/1974 | Yaroshuk et al. . |
| 3,852,600 | 12/1974 | Faulkner et al. ...................... 378/61 |
| 3,903,416 | 9/1975 | Fox . |
| 4,032,785 | 6/1977 | Green et al. ........................... 378/61 |
| 4,207,470 | 6/1980 | Heisner et al. . |
| 4,694,479 | 9/1987 | Bacskai et al. ....................... 378/58 |
| 4,785,354 | 11/1988 | Nakamura et al. ................... 378/61 |

FOREIGN PATENT DOCUMENTS

| | | | |
|---|---|---|---|
| 2264356 | 7/1974 | Fed. Rep. of Germany ........ 378/61 |
| 0191947 | 8/1986 | Japan .................................... 378/61 |

*Primary Examiner*—Carolyn E. Fields
*Assistant Examiner*—David P. Porta
*Attorney, Agent, or Firm*—Litman, McMahon & Brown

[57] ABSTRACT

A portable tire X-ray apparatus includes a frame having horizontal rollers supporting a tire vertically and a motor connected to at least one of the rollers to cause rotation of the tire. An X-ray tube and a fluoroscope are spaced apart approximately the length of the outer diameter of the tire and are aligned to irradiate an area including at least half the width of the tread and a portion of the sidewall of the tire. A video camera is optically coupled to the fluoroscope and is connected to a video tape recorder and a live video monitor to convert a radiographic image on the fluoroscope to a video signal which may be recorded and displayed on the monitor. Irregularities in the tire, including possible defects, are visible on the fluoroscope and may be viewed on the monitor and recorded. The video recorder is also provided with a video monitor such that live radiographic images may be displayed on the live monitor while previously recorded images are played back and displayed on the recorder monitor for comparison of the images to discover new irregularities in the tire.

19 Claims, 3 Drawing Sheets

U.S. Patent    Jun. 13, 1989    Sheet 1 of 3    4,839,914
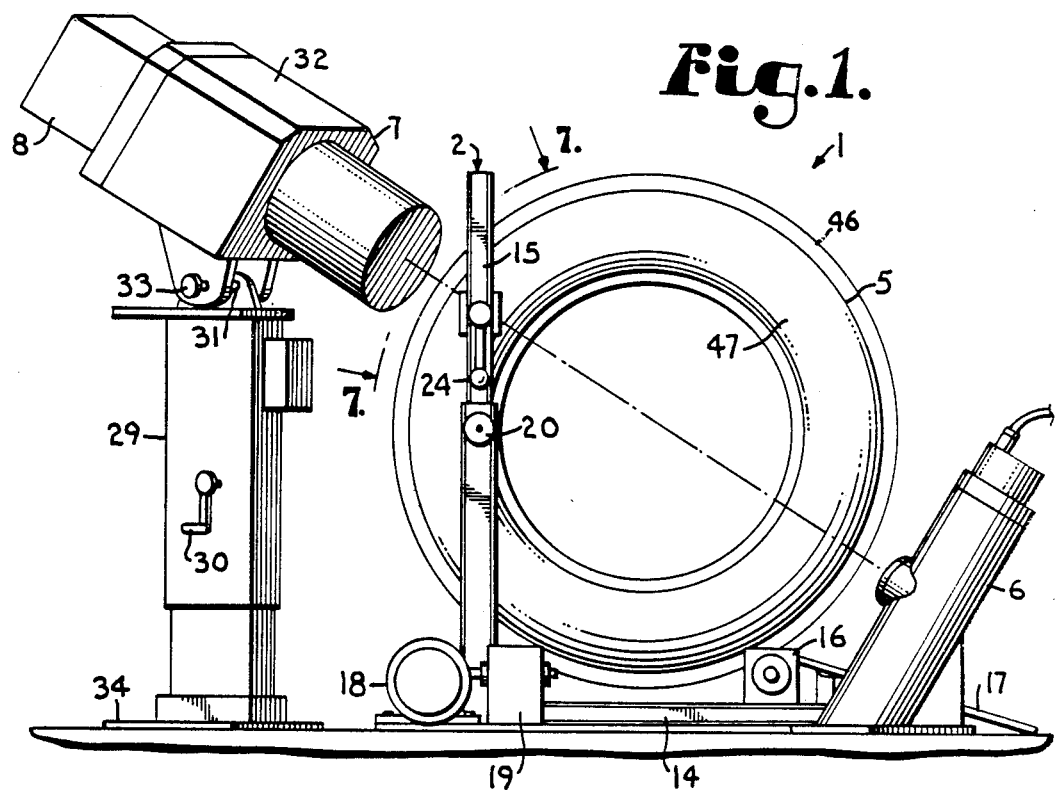
*Fig.1.*
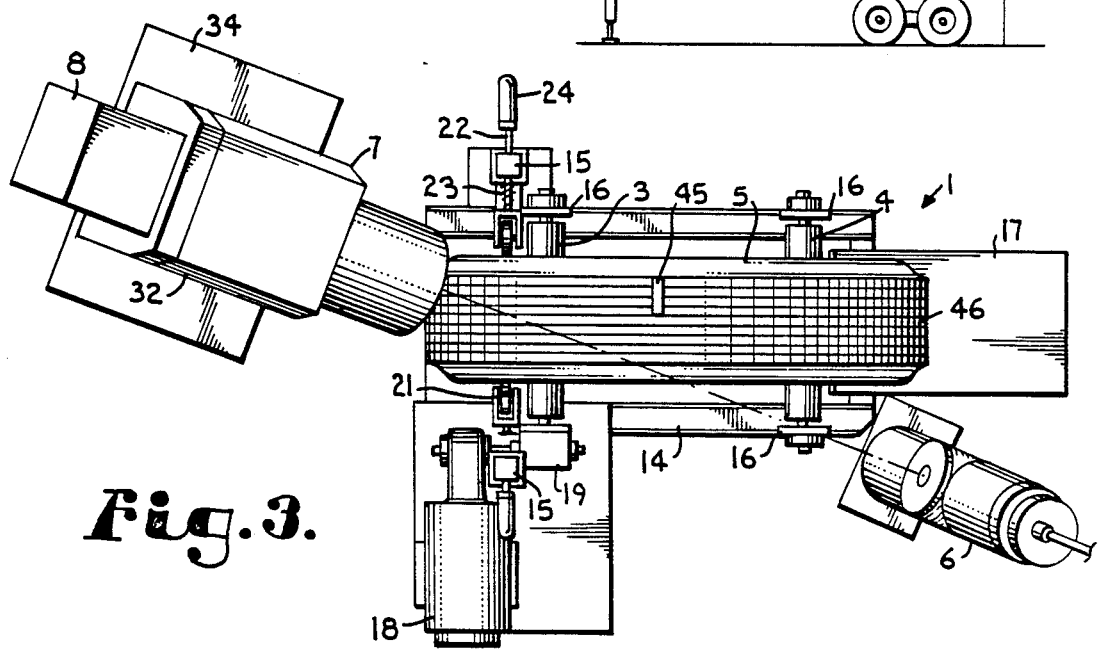
*Fig.2.*
*Fig.3.*

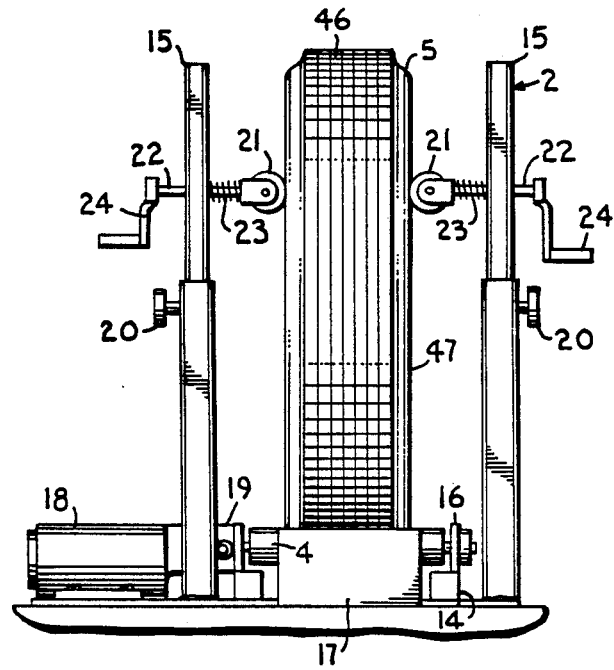
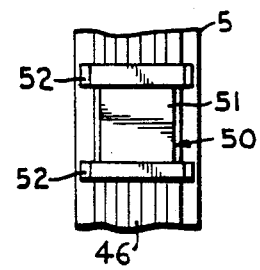
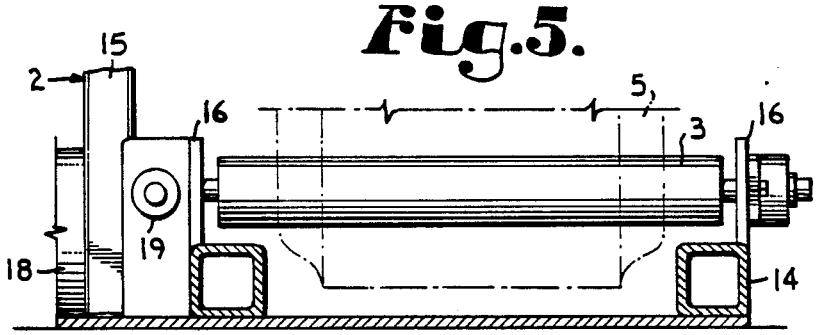
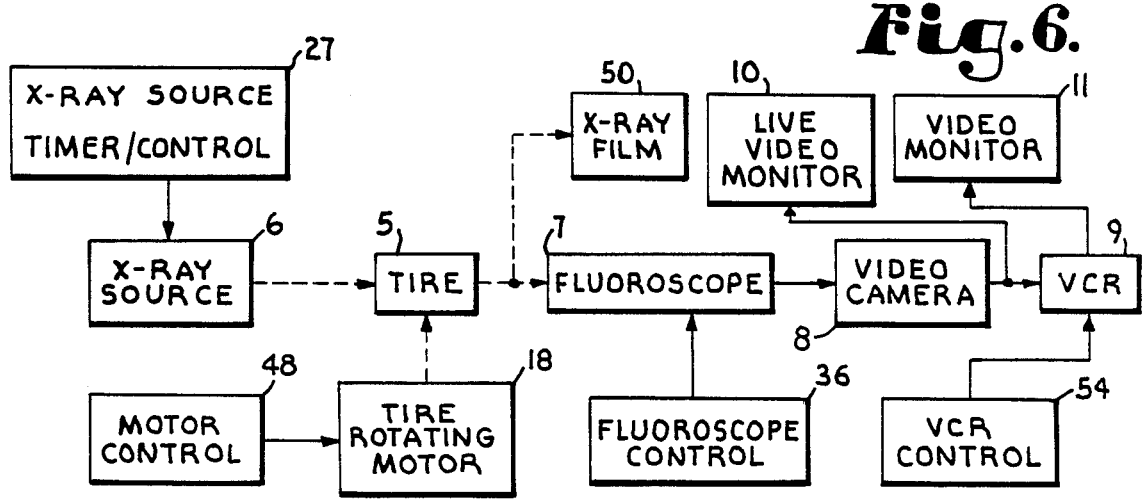

PORTABLE TIRE X-RAY APPARATUS AND METHOD

FIELD OF THE INVENTION

The present invention relates to tire inspection apparatus and methods and to such apparatus and methods which are particularly suited to the tire recapping industry.

BACKGROUND OF THE INVENTION

Various types of X-ray apparatus have been used in the past for the inspection of tires to discover defects not visible from viewable portions of tires. For the most part, such apparatus has been associated with automotive servicing or with the manufacture of tires. Apparatus installed in service stations and tire retailers are usually adapted for inspection of tires which are mounted on wheel rims for the discovery and location of defects incurred in use of the tires on the road for subsequent repair. In the tire manufacturing environment, tire makers universally use X-ray apparatus for quality control purposes to discover manufacturing defects.

In trucking operations involving medium and large trucks, it is a standard practice to recap or retread tires after a period of use in which the original tread is worn away. The reason for this is simple: medium and large truck tires are relatively expensive. In most cases, little damage occurs to truck tires in normal use such that the tires can be safely retreaded if undamaged tire carcasses are used. On the other hand, when a tire with defects is recapped, the tire can be completely destroyed under the pressures and temperatures which occur during normal use creating hazards to the driver and others on the road. A problem arises in determining if a tire carcass has been damaged in a manner that cannot be discerned by visual inspection of the carcass. While large punctures and damage to the rubber portions of a tire can often be found by visual inspection, small punctures and damage to the tire cords are not usually visible externally.

The hazards to humans from overexposure to penetrating radiation, such as X-rays, are more fully appreciated in current times than they were in the past. Thus, while various types X-ray apparatus for tire inspection in general automobile and specialized tire servicing establishments have been proposed, such apparatus is not in general use at present because of the need to provide specialized training to infrequent operators of such equipment, the expense of acquiring and maintaining such equipment, and the liabilities involved. In contrast, quality control and product liability prevention in tire manufacturing require that newly manufactured tires be closely inspected. Since X-ray inspection of tires in such a setting is an ongoing operation, the expense of the necessary equipment and the training of personnel can be more easily justified. As a result, the development of industrial tire X-ray equipment has continued while the development and availability of similar equipment suitable for small commercial users has lagged.

SUMMARY OF THE INVENTION

The present invention provides apparatus and methods for X-ray tire inspection which are particularly well adapted for tire retreading operations. The apparatus includes a frame having a ramp leading to a set of motorized rollers for rotating a tire carcass between an X-ray tube and a fluoroscope. A video camera is optically coupled to the fluoroscope and is connected to a live video monitor and to a video cassette recorder. As the tire is rotated, a radiographic image of the tire is displayed on the monitor. The images of the tire are video recorded for comparison with subsequently generated images of the tire after it has been recapped and placed back in service. The frame, X-ray tube, and fluoroscope are placed in an X-ray shielded enclosure which is preferably mobile, such as a trailer, to protect the operator from overexposure to X-rays.

The invention includes means to synchronize to display of previously recorded images with currently generated images of a tire. A radiopaque index tag with a serial number is placed on the tire in a standardized location, such as adjacent the serial number of a tire, and the inspection is conducted during a full rotation of the tire from a point at which the tag is visible on the monitor until it is again visible on the screen. When a defect is detected on the monitor screen, the rotation of the tire is stopped along with the video recorder, the X-ray tube is deactivated, a sheet of X-ray sensitive film is placed on the tire covering the area of the defect, and the film is exposed by activation of the X-ray tube to provide a photographic record of the defect. The area of the defect may be marked, such as with chalk, to facilitate repair if repair is feasible.

OBJECTS OF THE INVENTION

The principal objects of the present invention are: to provide an apparatus and methods for inspecting tires using X-rays to discover and locate defects; to provide such apparatus and methods which are particularly well adapted for use in connection with the retreading of tires; to provide such an apparatus including means for rotating a tire between an X-ray source and a fluoroscope, a video camera for generating video signals represent images formed on the fluoroscope, a video monitor for displaying the images, and a video recorder for recording and playing back the images; to provide such an apparatus which is portable or mobile, such as by mounting the apparatus in a trailer; to provide such an apparatus in a trailer which is X-ray shielded to prevent the leakage of X-rays and to prevent the overexposure of the operator by X-rays; to provide a method of operating such an inspection apparatus including the playback of previously generated radiographic images of a tire simultaneous with the display of images of a tire currently being generated for comparison to detect new defects in the tire; to provide such an apparatus in which the X-ray tube is positioned external to the tire under inspection to facilitate the placement of a tire on the inspection apparatus and to provide softer X-rays to increase the contrast of images generated by the apparatus; and to provide such an X-ray tire inspection apparatus and method which are economical to manufacture and practice, safe and effective, and which are particularly well adapted for their intended purpose.

Other objects and advantages of the present invention will become apparent from the following description taken in connection with the accompanying drawings wherein are set forth, by way of illustration and example, certain embodiments of this invention.

The drawings constitute a part of the specification, include an exemplary embodiment of the present invention, and illustrate various objects and features thereof.

BRIEF DESCRIPTION OF THE DRAWINGS

FIG. 1 is a side elevational view of a portable tire X-ray apparatus according to the present invention.

FIG. 2 is a side elevational view at a reduced scale of a shielded trailer with a portion of a wall removed to illustrate the tire X-ray apparatus installed therein.

FIG. 3 is a top plan view of the X-ray apparatus as illustrated in FIG. 1.

FIG. 4 is a fragmentary end elevational view of the X-ray apparatus.

FIG. 5 is a fragmentary enlarged end elevational view of the apparatus and illustrates details of rollers employed to rotate a tire during inspection.

FIG. 6 is a general block diagram illustrating components of the tire X-ray apparatus according to the present invention.

FIG. 7 is a fragmentary view taken generally along line 7—7 of FIG. 1 and illustrates an X-ray sensitive film pack for attachment to a tire during irradiation to provide a permanent record of a detected defect.

DETAILED DESCRIPTION OF THE PREFERRED EMBODIMENTS

Figure 8:
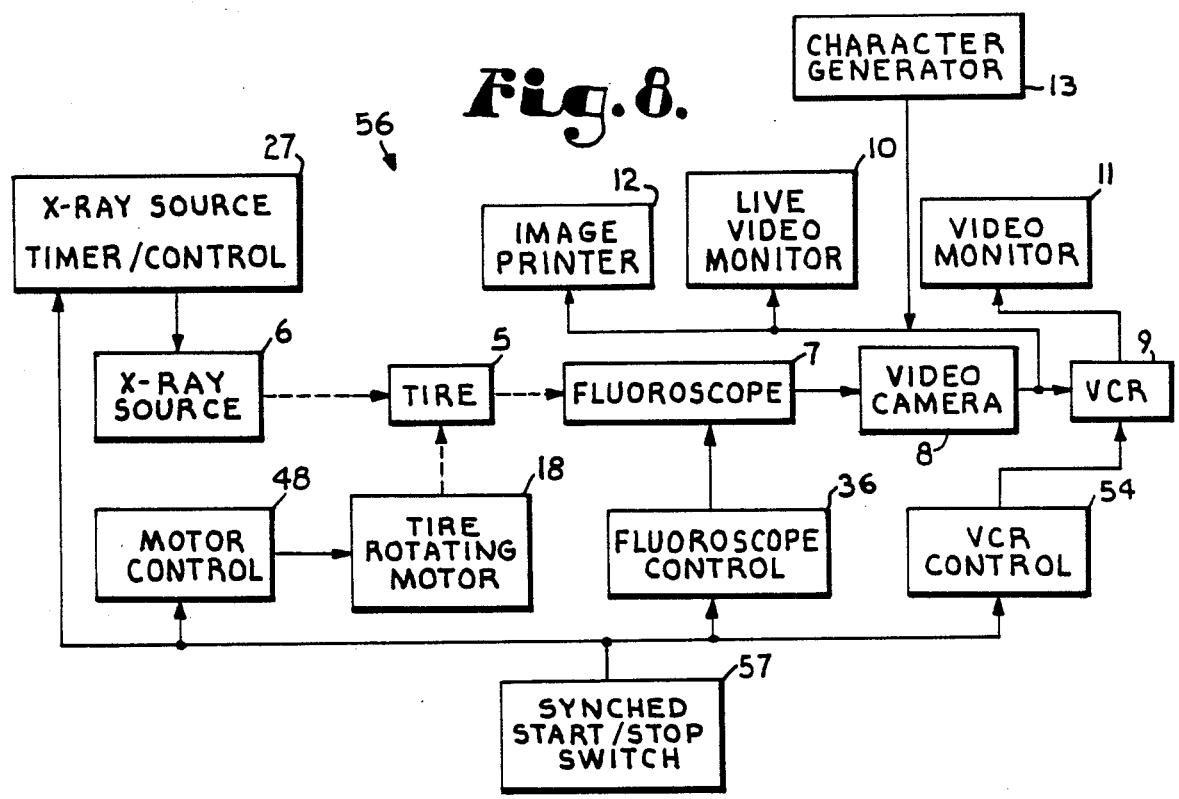
FIG. 8 is a block diagram of components of the tire X-ray apparatus and illustrates a synchronized start/stop switch for synchronizing the playback of previously recorded images of a tire with the display of currently generated images of the tire.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates an X-ray tire inspection apparatus according to the present invention. The apparatus 1 generally includes a frame 2 on which are journaled rollers 3 and 4 which cooperate with the frame to support and rotate a tire 5 between an X-ray source 6 and a fluoroscope 7 to irradiate the tire 5 and form radiographic images of the tire on the fluoroscope 7. A video camera 8 is optically coupled to the fluoroscope 7 and generates video signals representing the radiographic images formed on the fluoroscope. The camera 8 is connected to a video recorder/playback unit 9 (FIG. 6), such as a video cassette recorder (VCR) unit, to record the radiographic images for later study or for comparison with currently generated or live images of a tire 5. The camera S has a live video monitor 10 connected thereto for displaying live images while the VCR 9 has a recorder video monitor 11 connected thereto to display images being played back by the VCR 9. An image printer 12 (FIG. 8) may also be connected to the camera 8 to provide a hard copy record of video frames of interest. Additionally, a character generator 13 may be interconnected with the camera 8, VCR 9, and image printer 12 to cause the display of alphanumeric information on the video frames, such as the time, date, serial number of the tire, or the like.

The frame 2 includes a base 14 having tire guide standards 15 upstanding therefrom. Tabs 16 of the base provide for mounting the rollers 3 and 4 horizontally across the base 14. An inclined ramp plate 17 is provided on the base 14 and facilitates the rolling of a tire 5 onto the frame 2 for inspection. An electric motor 18 is mounted on the base 14 and is drivingly connected to one of the rollers, such as roller 3, through a gear unit 19 which may include right angle gear components Thus, roller 3 is a powered roller while roller 4 is an idler, although both rollers may be powered if desired. The tire guide standards 15 preferably telescope for vertical adjustment and include knobs 20 cooperating with bolts to clampingly fix the heights of the standards 15. The standards 15 have guide wheels 21 resiliently mounted thereon by shafts 22 having springs 23 sleeved thereon. The guide wheels 21 engaged a tire 5 on the frame 2 and maintain its vertical orientation during rotation of the tire 5. The shafts 22 are threaded into the standards 15 and are laterally adjustable by means of cranks 24 attached to the ends of the shafts 22 to vary the spacing between the guide wheels 21.

The X-ray source 6 is a conventional X-ray tube such as is used in other industrial radiographic applications. The X-ray tube 6 is connected to an X-ray source timer/control circuit 27 (FIG. 6) which includes a high voltage supply providing power in the range of 70 to 75 kilovolts at about three milliamperes. The source 6 is operated continuously during an inspection cycle as the tire 5 is rotated such that positive cooling of the tube 6 is advisable to prolong its life. As will be detailed below, when a tire defect is observed on the screen of the monitor 10, an X-ray film is exposed. During such exposure, the X-ray source timer/control 27 is adjusted to control the time of exposure.

The fluoroscope 7 includes a stand 29 which is preferably height adjustable. The illustrated stand 29 is formed of telescoping portions having means such as a rack and pinion (not shown) engaged therebetween which is actuated by a crank 30. Atop the stand 29 is a pivot mechanism 31 which connects a fluoroscope housing 32 to the stand 29. A knob 33 cooperates with the pivot mechanism 31 to clamp it in place when the housing 32 is pivoted to a desired position. A wide base plate 34 on the bottom of the stand 29 distributes the weight of the fluoroscope assembly and resist undesired tilting of the stand 29.

The fluoroscope 7 includes a screen (not shown) coated with phosphors which are illuminated upon irradiation by X-rays in proportion to the intensity of the X-rays incident on the screen. The fluoroscope 7 includes fluoroscope control circuitry 36 to provide power thereto and to allow control, for example, of the sensitivity and brightness and, to some extent, the contrast of the fluoroscope 7. The video camera 8 is mounted on the housing 32 of the fluoroscope 7 and is optically coupled in such a manner that the image formed on the fluoroscope screen is scanned by the camera 8 and converted to a video signal. The camera 8 is connected to the live video monitor 10 and the VCR 9 such that the video signal is reconverted to a radiographic image and displayed on the monitor 10 and is recorded for subsequent playback by the VCR 9.

The apparatus 1 is preferably portable and, in the illustrated embodiments, is housed in a trailer 39 (FIG. 2). The trailer 39 may be any suitable vehicle, such as a mobile home type vehicle or, as illustrated, a small truck type trailer. The trailer 39 has X-ray shielded external walls 40 to prevent the leakage of X-rays external to the trailer 39. The external walls 40 may be shielded as by the incorporation of lead panels or plates (not shown) therein. In order to prevent overexposure of an operator of the apparatus 1 by X-rays, an operator compartment or room 41 is formed within the trailer 39 as by an X-ray shielded wall 42 between the operator's compartment 41 and the remainder of the trailer 39 having the apparatus 1 therein. The wall 42 has lead panels or plates (not shown) or other shielding material incorporated therein. The will 42 is provided with a leaded window 43 to allow the operator to view the apparatus 1 during operation without risking exposure by X-rays.

In operation, a tire 5 not mounted on a wheel is rolled into the trailer 39 up the ramp 17, and onto the rollers 3 and 4 of the tire inspection frame 2. A radiopaque index tag 45, preferably having a serial number marked thereon or stenciled therein, is placed on the tread 46 of the tire 5 in a standardized location to identify the tire and to signal the beginning and end of an inspection rotation cycle. The serial number on the tag 45 is visible on the live video monitor 10 during irradiation. A standardized location on the tire 5 may be, for example, in radial alignment with the valve stem of a tubeless tire, in alignment with a manufacture's serial number imprinted on a sidewall 47 of the tire 5, or the like. Depending on the stiffness of the tire carcass, it might be necessary to provide some means of holding the sidewalls 47 in spread apart relation to assure that the tread 46 is clearly irradiated. The sidewalls 47 may be held open by means such as wooden dowels (not shown) or by other radio-transparent rods or the like inserted between the sidewalls 47.

As illustrated in FIGS. 1 and 3, the X-ray tube 6 and fluoroscope 7 are positioned in alignment to irradiate an area slightly greater than the width of the tread 46 and a portion of the sidewall 47 of the tire 5 as it is rotated between the X-ray tube 6 and the fluoroscope 7. As shown, particularly in FIG. 1, the X-ray tube 6 and fluoroscope 7 are spaced apart approximately the length of the outer diameter of the tire 5. This has two principal advantages. The placement of the X-ray tube 6 external to the tire 5 and somewhat to the side of the base 14 of the frame 2 allows more convenient loading of a tire 5 onto the frame 2 and unloading since the X-ray tube 6 does not interfere. Additionally, the placement of the X-ray tube 6 at such a distance from the fluoroscope 7 causes "softer" X-rays to expose the fluoroscope for a given operating voltage resulting in an image having greater contrast. The reason for this is that the softer rays are less penetrating to the materials of the tire 5 whereby there is a greater difference in absorption of the X-rays by the different materials and thicknesses thereof. Thus, more tire structure detail is visible.

When the tire 5 has been properly positioned and prepared, the fluoroscope 7 is activated through the fluoroscope control 38, and the video camera 8 and live video monitor 10 are activated. Initially, the tire 5 may be irradiated and inspected by viewing the live monitor 10 to discover and locate any defects in the tire 5, such as previously undiscovered punctures or broken or distorted cords. For this, the motor 18 is activated by a motor control 48, thereby rotating the tire between the X-ray tube 6 and the fluoroscope 7. The X-ray tube 6 is activated to irradiate the fluoroscope 7 through the tire 5, and a radiographic image is formed on the fluoroscope 7 which is scanned by the camera 8 and converted to a video signal. The video signal is reconverted to an image by the live video monitor 10 which may be viewed by the operator as the tire is rotated. If an irregularity is detected, the motor 18 is deactivated and, if reversible, may be manipulated to place the irregularity on the screen of the monitor 10 stationarily for a closer inspection.

If through the experience of the operator the irregularity appears to be a defect or damage, the X-ray tube 6 is deactivated, and the operator leaves the shielded compartment 41 and attaches an X-ray sensitive film pack 50 (FIG. 7) on the tread 46 of the tire 5 in the area covered by the fluoroscope 7. The film pack 50 may consist of a piece of X-ray sensitive film 51 in a light impervious envelop (not shown) with an adhesive applied thereto. Alternatively, strips of an adhesive tape 52 may be provided on the film pack 50. At the same time, the area of the defect is preferably marked, as with chalk, so that the defect can be subsequently found and repaired, if necessary or possible. The operator re-enters the compartment 41 and causes a timed X-ray exposure of the film through the defect to occur by operation of the X-ray timer/control 27. The X-ray film 51 will be developed later to provide documentation of the defect. X-ray films generally provide much higher resolution detail than either fluoroscopic images or video images created therefrom. The operator may also cause a video image to be printed by activation of the image printer 12. The image printer 12 may, for example, be a device such as a model UP-811 or UP-701 video graphic printer manufactured by Sony Medical Products Company of Hackensack, New Jersey. Alternatively, other types of hard copy imaging devices may be employed.

After the tire 5 has been inspected through one complete rotation, the tire 5 is flipped around to inspect the other side. This is because the X-ray tube 6 and fluoroscope 7 are positioned angularly relative to the tire 5 to inspect an area having a width slightly greater than half the width of the tread 46 and a portion of the sidewall 47 at a time. Thus, the tire 5 must be turned around to fully inspect the entire carcass of the tire 5.

After all such irregularities are studied and documented, if appropriate, the radiographic images of the tire 5 are video recorded. A video cassette (not shown) is placed in the video cassette recorder (VCR) 9, and the tire 5 is rotated such that the index tag 45 is aligned between the X-ray tube 6 and the fluoroscope 7. The operator then enters the compartment 41 and activates the X-ray tube 6, the fluoroscope 7, the VCR 9 by means of a VCR control unit 54, and the motor 18. The rotation and irradiation of the tire 5 is continued at least until the index tag 45 reappears on the screen of the live video monitor 10, at which time the operation may be terminated. The video recording thus produced may be used for later comparison with a live generation of radiographic images of the same tire 5 for comparison purposes. During the display of images on the monitor 10 and during the recording of the images by the VCR 9, the character generator 13 is preferably activated to display identifying alphanumeric information on the images. The character generator 13 may be similar to that used in association with the AFP Satellite B10 series of video imaging devices which are manufactured by the AFP Imaging Corporation of Elmsford, N.Y.

After inspection, the tire 5, if new, is mounted on a rim, installed on a truck, and placed into service. If the tire is not new but is of adequate quality, it is recapped and placed in service. Otherwise, if the carcass of the tire 5 is too badly damaged for safe recapping, it is disposed of in an appropriate manner. After the tread 46 of the tire 5 is worn down by use on the road and before recapping again, it is once more inspected in the manner described above. As the tire 5 is reinspected, previously generated radiographic images of the tire are played back on the VCR 9 and viewed on the recorder video monitor 11 as current radiographic images of the tire 5 are generated and displayed on the live video monitor 10. As the sets of images are played on the monitors 10 and 11, preferably in substantial synchronism for comparison of corresponding sectors of the tire 5, the differences in the images facilitate the discovery of any new irregularities or defects in the tire 5 from use on the road.

FIG. 8 illustrates an embodiment of the apparatus 1 for synchronzing the generation of live radiographic images of a tire 5 with the playback of previously recorded images of the same tire. The synchronized tire inspection control system 56 includes the same components as shown in FIG. 6 with the addition of a synchronized start/stop switch 57. The switch 57 is connected to the X-ray source timer/control circuit 27, the motor control 48, the fluoroscope control 36, and the VCR control 54. In operation of the system 56, the tire 5 is rotated to locate the index tag 45 in alignment between the X-ray tube 6 and the fluoroscope 7; and the VCR 9 is operated by use of the VCR control 54 to position the video tape at a position displaying the index tag 45 on the recorder video monitor 11.

Upon operation of the switch 57, the X-ray tube 6, the motor 18, the fluoroscope 36, and the VCR 9 in the playback mode are all activated simultaneously. By this means, the previously recorded radiographic images are played back simultaneous with the generation of current images of the tire 5. The motor 18 is operated at a relatively slow speed such that it takes approximately one and a half minutes for a complete rotation of the tire 5. Therefore, there is no requirement for absolute synchronism between the old and new images. It is only necessary that there be sufficient synchronism between the sets of images for comparative viewing of corresponding sectors of the tire 5.

Figure 9:
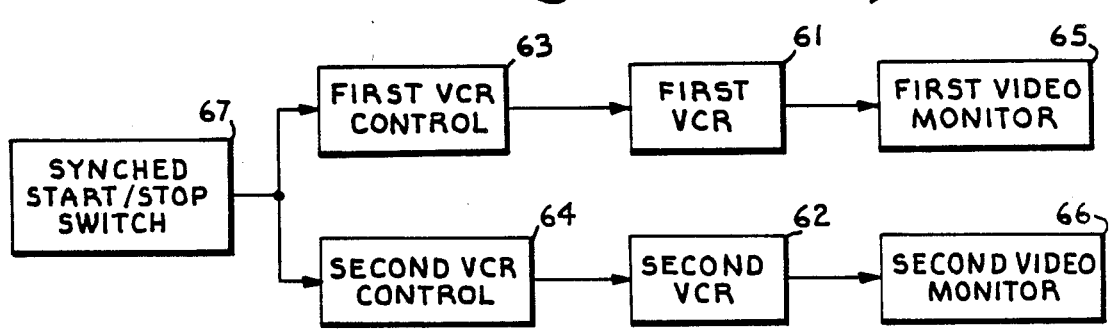
FIG. 9 is a block diagram illustrating the synchronized playback of two sets of radiographic images of a tire which have been recorded using the tire X-ray inspection apparatus according to the present invention.

FIG. 9 illustrates an alternative synchronized tire image viewing system 60 for simultaneous viewing of two sets of radiographic images of a tire 5. The system 60 employs two VCR's 61 and 62 controlled by respective VCR controls 63 and 64 and displaying images on respective recorder video monitors 65 and 66. A synchronized start/stop switch 67 is connected to the first and second VCR controls 63 and 64 and activates them simultaneously. In the system 60, the sets of images of the tire 5 are recorded as described above on separate tape cassettes for simultaneous playback on the VCR's 61 and 62. For simultaneous playback, each of the VCR's is operated by its respective VCR control 63 or 64 to position its tape such that the starting image of the index tag 45 is displayed. Then, the switch 67 is operated to activate the playback mode of the VCR's 61 and 62 simultaneously. The VCR's 61 and 62 may be stopped simultaneously when the ending images of the index tags are viewed by again operating the switch 67.

The present invention provides advantageous apparatus and methods for X-ray inspection of tires and for developing histories of individual tires throughout their service life. Trucking companies, especially smaller firms, often cannot justify the expense of such tire inspection equipment. However, the placement of the apparatus 1 in the trailer 39 allows an independent contractor with such equipment and appropriate training to service a number of trucking companies and additionally companies which acquire and retread used tire carcasses.

It is to be understood that while certain forms of the present invention have been described and illustrated herein, it is not to be limited to the specific forms or arrangement of parts described and shown.

What is claimed and desired to be secured by letters patent is as follows:

1. A tire inspection apparatus comprising:
    (a) a frame supporting a tire during inspection;
    (b) tire rotation means drivingly engaged with a tire supported on said frame and activated to cause rotation of said tire during inspection thereof;
    (c) a fluoroscope positioned adjacent a tread of a tire supported on said frame and forming an image upon the irradiation of said fluoroscope by X-rays;
    (d) an X-ray source aligned with said fluoroscope, said source positioned external to a tire on said frame and spaced from said fluoroscope substantially the length of a diameter of a tire on said frame;
    (e) a video camera optically coupled to said fluoroscope to generate a video signal representing a radiographic image formed on said fluoroscope;
    (f) a first video monitor operatively connected to said video camera and comprising means for displaying an image represented by said video signal
    (g) a video recorder interconnected with said video camera for recording radiographic images of a tire supported on said frame during inspection of the tire; and
    (h) a second video monitor interconnected with said video recorder and comprising means for displaying previously recorded radiographic images of a tire taken at an earlier time for direct visual comparison to currently generated radiographic images of the same tire displayed on said first video monitor.

2. An apparatus as set forth in claim 1 including:
    (a) a sheet of X-ray film positioned in alignment with said X-ray source on an opposite side of a tire supported on said frame for exposure by irradiation through said tire to provide a photographic record of a radiographic image of a portion of said tire.

3. An apparatus as set forth in claim 1 including:
    (a) a mobile trailer having said apparatus housed therein such that said apparatus is portable.

4. An apparatus as set forth in claim 5 including:
    (a) X-ray shield means positioned within said trailer between said video monitor and the remainder of said apparatus to protect an operator viewing said monitor during the irradiation of a tire supported on said frame.

5. An apparatus as set forth in claim 1 wherein said tire rotation means includes:
    (a) a pair of horizontally oriented rollers journaled on said frame in spaced apart relation and supporting a tire on said frame; and
    (b) a rotary motor drivingly engaged with at least one of said rollers to rotate same to cause rotation of a tire engaged with said rollers.

6. An apparatus as set forth in claim 1 including:
(a) tire guide means upstanding from said frame and engaging a tire on said frame to position and maintain an axis of rotation of said tire horizontally during rotation of said tire.

7. An apparatus as set forth in claim 1 including:
(a) a ramp formed on said frame to facilitate the rolling of a tire onto said frame for inspection.

8. An apparatus as set forth in claim 1 including:
(a) image printer means operatively interconnected with said video camera and operative to form a hard copy record of a radiographic image of a portion of said tire.

9. A method of inspecting a tire using an X-ray source, a fluoroscope aligned with said source, a video camera optically coupled with said fluoroscope, a video recorder connected to said camera, a live video monitor connected to said camera and a recorder video monitor connected to said video recorder, and means rotating an annular portion of said tire between said X-ray source and said fluoroscope, said method comprising the steps of:
(a) rotating an annular portion of a tire between an X-ray source and a fluoroscope;
(b) irradiating said annular portion of a tire by activation of said X-ray source to generate on said fluoroscope first radiographic images of said tire;
(c) generating by a video camera first video signals representing said first radiographic images of said tire;
(d) recording said first video signals by a video recorder/playback unit;
(e) after said tire has been in service for a period of time, rotating an annular portion of said tire between said X-ray source and said fluoroscope;
(f) irradiating said annular portion of said tire by activation of said X-ray source to generate on said fluoroscope second radiographic images of said tire;
(g) generating by said video camera second video signals representing said second radiographic images of said tire;
(h) displaying said second radiographic images on a live video monitor connected to said video camera;
(i) playing back the previously recorded first video signal representing said first radiographic images of said tire simultaneous with said displaying said second radiographic images;
(j) during said playing back step, displaying said first radiographic images on a recorder video monitor connected to said video recorder/playback unit; and
(k) visual comparing said first and second radiographic images of said tire to discover any new defect in said tire from placement of said tire in service.

10. A method as set forth in claim 9 including the step
(a) displaying said first radiographic images on a live video monitor connected to said camera during the generation of said first radiographic images by said fluoroscope.

11. A method as set forth in claim 10 including the step of:
(a) substantially synchronizing the generation and display of said second radiographic images with the playback and display of said first radiographic images for visual comparison of corresponding sectors of said tire.

12. A method as set forth in claim 10 including the steps of:
(a) placing a radiopaque index tag at a selected location on an annular portion of a tire to be irradiated, said index tag being visible on said live video monitor;
(b) recording said first video signals while rotating said tire at least a complete revolution beginning and ending at said index tag;
(c) upon irradiating said tire to generate said second video signals, replacing said index tag at said selected location on said annular portion of said tire;
(d) positioning said tire at said index tag and initiating rotation of said tire to generate and display said second radiographic images; and
(e) initiating the playback of said first radiographic images a the previously recorded image of said index tag such that said first and second radiographic images are displayed in substantial synchronism for visual comparison of corresponding sectors of said tire.

13. A method as set forth in claim 10 including the steps of:
(a) upon detecting a defect in said tire by viewing said first or second radiographic images on said live video monitor, stopping the rotation of said tire, stopping the recording of first video signals, and deactivating said X-ray source;
(b) removably attaching a piece of X-ray sensitive film on said tire covering an area of said tire encompassing said defect; and
(c) activating said X-ray source to irradiate said film through said defect such that a photographic image of said defect is produced on said film.

14. A method as set forth in claim 9 including the steps of:
(a) printing a hard copy record of a radiographic image of a portion of said tire by activating image printer means interconnected with said video camera.

15. A method of inspecting a tire using an X-ray source, a fluoroscope aligned with said source, a video camera optically coupled with said fluoroscope, a pair of video recorders, one of said video recorders connected to said camera, a live video monitor connected to said camera, a recorder video monitor connected to each video recorder, and means rotating an annular portion of said tire between said X-ray source and said fluoroscope, said method comprising the steps of:
(a) rotating an annular portion of a tire between said X-ray source and a fluoroscope;
(b) irradiating said annular portion of a tire by activation of said X-ray source to generate on said fluoroscope first radiographic images of said tire;
(c) generating by a video camera first video signals representing said first radiographic images of said tire;
(d) recording said first video signals by a first video recorder/playback unit;
(e) after said tire has been in service for a period of time, rotating an annular portion of said tire between said X-ray source and said fluoroscope;
(f) irradiating said annular portion of said tire by activation of said X-ray source to generate on said fluoroscope second radiographic images of said tire;

(g) generating by said video camera second video signals representing said second radiographic images of said tire;

(h) recording said second video signals by said first video recorder/playback unit;

(i) simultaneously playing back each of the previously recorded first and second video signals on of said first video recorder/playback unit and a second video recorder/playback unit;

(j) during said playing back step, simultaneously displaying said first and second radiographic images respectively on a pair of recorder video monitors associated respectively with said first and second video recorder/playback units; and (k) visually comparing said first and second radiographic images of said tire to discover any new defect in said tire from placement of said tire in service.

16. A method as set forth in claim 15 including the step of:

(a) substantially synchronizing the playback and display of said second radiographic images with the playback and display of said first radiographic images for visual comparison of corresponding sectors of said tire.

17. A method as set forth in claim 15 including the step of:

(a) displaying a respective set of said first and second radiographic images on a live video monitor connected to said camera during the generation of said set of radiographic images by said fluoroscope.

18. A method as set forth in claim 17 including the steps of:

(a) placing a radiopaque index tag at a selected location on an annular portion of a tire to be irradiated, said index tag being visible on said live video monitor;

(b) recording said first video signals while rotating said tire at least a complete revolution beginning and ending at said index tag;

(c) upon irradiating said tire to generate said second video signals, replacing said index tag at said selected location on said annular portion of said tire;

(d) recording said second video signals while rotating said tire at least a complete revolution beginning and ending at said index tag; and (e) simultaneously initiating the playback of said first and second radiographic images at the previously recorded images of said index tag such that said first and second radiographic images are displayed in substantial synchronism for visual comparison of corresponding sectors of said tire.

19. A tire inspection apparatus comprising:

(a) a frame including a base;

(b) a pair of horizontally oriented rollers journaled on said base in spaced apart relation positioned such that when said apparatus is in use, said rollers are positioned so as to be in proximity to but spaced from a supporting floor surface;

(c) tire guide means upstanding from said frame to support a tire on said rollers with an axis of rotation of the tire positioned horizontally; said guide means including a pair of standards secured to said base and extending upwardly therefrom; each of said standards including thereon roller means for engaging and supporting a tire while allowing such a tire to rotate on said rollers;

(d) rotary motor means drivingly engaged with at least one of said rollers and activated to rotate same to cause rotation of a tire engaged therewith;

(e) a ramp positioned to extend between said rollers and the floor surface; said ramp aligned with said rollers so as to comprise means for facilitating the rolling of a tire onto said rollers from the floor surface by rolling of the tire by an operator;

(f) a fluoroscope positioned adjacent a tread of a tire supported on said frame and forming an image upon the irradiation of said fluoroscope by X-rays;

(g) an X-ray source oriented in alignment with said fluoroscope, said source positioned external to a tire on said frame and spaced from said fluoroscope substantially the length of a diameter of a tire on said frame;

(h) a video camera optically coupled to said fluoroscope to generate a video signal representing an image formed on said fluoroscope;

(i) a first video monitor operatively connected to said video camera and comprising means for displaying an image represented by said video signal;

(j) a video recorder interconnected with said video camera and recording radiographic images of a tire supported on said frame during the inspection of said tire; and (k) a second video monitor interconnected with said video recorder, positioned adjacent said first video monitor, said second video monitor comprising means for displaying previously recorded radiographic images of a tire while said first video monitor displays currently generated radiographic images of the same tire supported on said frame and undergoing irradiation, for comparison purposes.

* * * * *